United States Patent [19]

Forte

[11] Patent Number: 5,563,315
[45] Date of Patent: Oct. 8, 1996

[54] SEPARATION OF AROMATIC HYDROCARBONS FROM A MIXTURE OF AROMATIC AND NON-AROMATIC HYDROCARBONS BY SOLUTE SWING EXTRACTION

[75] Inventor: Paulino Forte, Yonkers, N.Y.

[73] Assignee: UOP, Des Plaines, Ill.

[21] Appl. No.: 173,856

[22] Filed: Dec. 22, 1993

[51] Int. Cl.⁶ .................. C07C 7/10; C07C 7/00
[52] U.S. Cl. .................. 585/835; 585/864; 585/866
[58] Field of Search .................. 585/835, 864, 585/866

[56] References Cited

U.S. PATENT DOCUMENTS

| | | | |
|---|---|---|---|
| 2,079,885 | 5/1937 | Voorhees | 196/13 |
| 2,342,205 | 2/1944 | Manley | 196/13 |
| 2,773,005 | 12/1956 | Meyer et al. | 196/14.17 |
| 3,291,728 | 12/1966 | Boyum et al. | 208/323 |
| 3,600,302 | 8/1971 | Hong | 208/321 |
| 3,788,980 | 1/1974 | Kubek et al. | 208/333 |
| 3,883,420 | 5/1975 | Stone | 208/321 |
| 3,985,644 | 10/1975 | Eberly, Jr. | 208/321 |
| 4,781,820 | 11/1988 | Forte | 208/333 |
| 5,022,981 | 6/1991 | Forte | 208/334 |

OTHER PUBLICATIONS

Hydrocarbon Processing, vol. 71, No. 11, Nov. 1992, p. 195.
Hydrocarbon Processing, vol. 67, No. 9, Sep. 1988, p. 89.

Primary Examiner—Sharon Gibson
Attorney, Agent, or Firm—Thomas K. McBride; John G. Tolomei; Richard P. Silverman

[57] ABSTRACT

The invention relates to a process for separating aromatic hydrocarbons from a mixed hydrocarbon feed employing a selective solvent which exhibits a low critical solution temperature of the solvent with a solute. The mixed hydrocarbon feed is passed to an extraction zone wherein the feed is contacted with a lean solvent to provide a raffinate stream comprising non-aromatics and a rich solvent stream comprising aromatics and solvent. Both the raffinate stream and the rich solvent stream are admixed with a sufficient amount of a solute at a temperature which is at or below a low critical solution temperature with the solvent to separate the raffinate and aromatic phases from the solvent/solute mixture. The solvent/solute mixture is heated to a separation temperature which is above the low critical solution temperature to provide a solvent phase which is essentially free of solute at energy levels significantly lower than conventional processes.

26 Claims, 1 Drawing Sheet

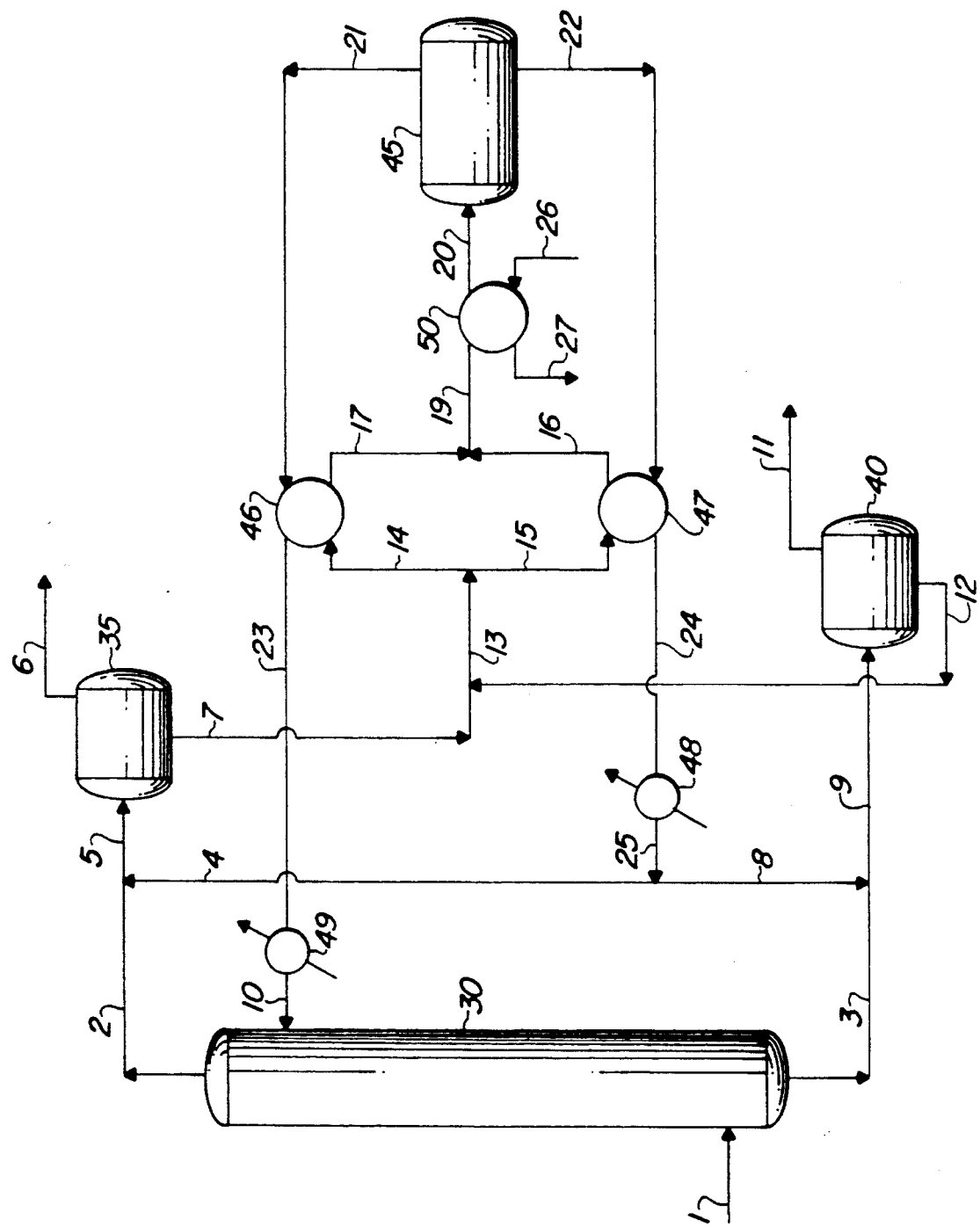

SEPARATION OF AROMATIC HYDROCARBONS FROM A MIXTURE OF AROMATIC AND NON-AROMATIC HYDROCARBONS BY SOLUTE SWING EXTRACTION

FIELD OF INVENTION

This invention relates to a process for the separation of aromatic and non-aromatic hydrocarbons from a mixed hydrocarbon feed, and more particularly, to the separation of aromatic and non-aromatic hydrocarbons with a selective solvent which forms a low critical solution temperature with a solute such as water. The process significantly decreases the overall energy requirement to separate the solvent from the solute phase to produce the aromatic product or to remove aromatic impurities such as polynucleararomatic compounds from petroleum distillates.

BACKGROUND OF THE INVENTION

The separation of aromatic and non-aromatic hydrocarbons (generally referred to as dearomatization) from mixed hydrocarbon feeds has long been recognized as necessary and advantageous for a number of varied reasons. For example, when a BTX fraction (benzene, toluene and xylene) is the aromatic fraction it may be used as a raw material in the manufacture of petrochemicals, or as an additive for gasoline to increase its octane rating. Further, the non-aromatic fraction derived from these mixed feeds have varied uses as fuels, solvents and the like and, therefore, are also highly desirable. Such uses for the aromatic and non-aromatic fractions have resulted in the development of numerous dearomatization processes.

Other aromatic hydrocarbons include those referred to as polynuclear aromatics (PNA's) are considered to be impurities in the hydrocarbon feed and the removal of PNA's from hydrocarbon mixtures containing such materials is typically energy intensive. The removal of PNA's from hydrocarbon feedstocks such as kerosine, diesel fuel and lubricating (lube) oils may be required to improve the physical properties of the material.

Of particular interest and difficulty is the separation of the complex components present in lube oils, wherein the removal of aromatic hydrocarbons is necessary to improve the viscosity index, thermal and oxidation stability, and color of the lube oils. The presence of aromatic hydrocarbons in lube oils affects the quality of these oils due to the low viscosity index, poor thermal and oxidation stability, high carbon residue, and poor color of such aromatic hydrocarbons. The aromatic hydrocarbons present in lube oils differ significantly from the BTX fraction found in light hydrocarbon mixtures used in the production of gasoline and, as a result, present vastly different separation problems.

Various processes have been suggested for the separation of the aromatic and non-aromatic hydrocarbons of a mixed feed wherein the aromatic is a BTX fraction. Typical of these processes is a process employing an extraction column for separation of a BTX fraction wherein a selective solvent, BTX and a reflux stream is introduced to a two step distillation column. BTX is then distilled to remove water and entrained solvent. Similarly, a process has been suggested wherein two distillation columns are employed with the BTX fraction and water being distilled in the second column. In addition, a process using two distillation columns wherein the second column is employed to distill the BTX fraction and other components, has been suggested.

One goal of the prior art has related to developing a dearomatization process which lowers the cost of dearomatization. Cost reduction for dearomatization processes can be achieved by improving the selectivity of the selective solvent and by modification of the separation process scheme. U.S. Pat. No. 3,985,644 mentions one such method for modifying the process scheme and reducing dearomatization costs, i.e., by reducing the use of energy-intensive steps, e.g., distillation.

In other attempts to reduce the energy of the dearomatization a mixed hydrocarbon feed, temperature swing processes were employed with a single extraction solvent or a mixed extraction solvent. These temperature swing processes were characterized by extraction at elevated temperature followed by separation at a lower temperature. The solvents employed in these temperature swing processes exhibited the formation of an upper critical solution temperature (UCST) with solutes, such that as the temperature of the solution is raised, the solute becomes more and more soluble in the solvent. This increase in solubility continues until the UCST is reached, at which point, both phases, the solute and the solvent phases are soluble in one another, in all proportions. This phenomenon permits aromatic component of the mixed hydrocarbon feed, now concentrated in the rich solvent stream, following an extraction step to be separated by cooling the rich solvent and by fractionation to separate the aromatic extract from the solvent phase. U.S. Pat. No. 4,781,820, which is hereby incorporated by reference, illustrates this concept in a process which contacts a hydrocarbon feed containing aromatic and non-aromatic hydrocarbons with a mixed extraction solvent and water in an extraction zone to provide a rich solvent stream comprising aromatics. The rich solvent stream following the removal of the extract phase is subsequently separated by distillation to provide the dry lean solvent phase required as the feed to the extraction zone and a water phase. Others as in U.S. Pat. No. 5,022,981 have employed steam distillation, extractive distillation, and combinations thereof to obtain a separation which produces the raffinate and extract products as well as the lean solvent.

The dearomatization of lube oils is of particular interest. Dearomatized lubricating oils are, generally speaking, naphthenic- and or paraffinic-type viscous materials having a low rate of viscosity change with change in temperature, i.e., relatively high viscosity index, a high degree of thermal and oxidation stability, low carbon-forming tendency, good color, and high flash points. Lubricating oil feedstocks are generally recovered as distillates or bottoms from the vacuum distillation of crude oils. A crude lube oil fraction contains many different chemical components, e.g., paraffins, naphthenes, aromatics, and the like. In order to obtain refined lubricating oils of relatively good quality and high viscosity index, the practice has been to remove components, such as aromatic and polyaromatic compounds, which tend to lower the viscosity index of the lube oil. The removal of these aromatic components has heretofore been carried out by processes as above-described and processes such as disclosed in U.S. Pat. Nos. 2,079,885; 2,342,205; 3,600,302; 2,773,005; 3,291,728; 3,788,980; and 3,883,420.

A number of selective extraction processes are commercially practical for treating lubricating oils to improve the quality of the hydrocarbon feedstock. Typically these hydrocarbon feedstocks comprise distillate stocks having boiling points above about 288° C. (550° F.). Three well-known processes for such extraction of raw lube stocks are EXXON - Exol N Extraction, as described in *Hydrocarbon Processing*, Vol. 71, No. 11, November 1992, page 195, TEXACO

- MP Refining, and TEXACO - Furfural Refining, as described in *HYDROCARBON PROCESSING*, Vol. 67, No. 9, September 1988, page 89. The following table contains the approximate energy consumption for a typical extraction plant processing 5,000 barrels per day of raw lube oil feedstock:

|  | kJ | (MMBTU/HR) |
|---|---|---|
| EXXON - EXOL N Extraction | 34.2 | 32.4 |
| TEXACO - MP Refining | 21.3 | 21.2 |
| TEXACO - Furfural Refining | 32.0 | 30.3 |

Processes are sought which can provide for the separation of aromatic hydrocarbons from mixtures with non-aromatic hydrocarbons by a method which is more economically advantageous or energy efficient and which overcomes the requirement for a distillation step to prepare the aromatic selective solvent for use in the extraction zone.

It is a further object of this instant invention to significantly reduce the amount of energy required to perform extraction of PNA's from lube feedstocks to improve the indices of quality in lube stocks such as viscosity index, color, etc.

SUMMARY OF THE INVENTION

The instant process relates to the discovery of a group of solvents which exhibit a low critical solution temperature (LCST) with a solute, such as water, and can be employed to extract hydrocarbon aromatic compounds from a mixture of hydrocarbon aromatic and non-aromatic compounds. These solvents display an inverted solubility profile with a solute such that when the LCST solvent and water are at or below the LCST, the solvent and the water are completely soluble in each other in all proportions; however, upon heating, the solute, or water, comes out of solution. PNA's and hydrocarbons are insoluble in water. In processes for extracting aromatics from a hydrocarbon mixture of aromatic and non-aromatic compounds, the extraction of the aromatics is performed in an extraction zone by contacting the mixture with a solute-reduced solvent to produce a solvent rich stream comprising aromatics and a raffinate depleted in aromatics. The separation of the hydrocarbon phase from the solvent phase is achieved by adding a solute to the streams at or below the low critical solution temperature. The separation of the solvent from the solute is accomplished by a simple heating step, instead of a distillation step. The substitution of the heating step for a distillation step to separate the solvent from the solute can result in a significant energy and equipment saving. For example, a 5,000 barrel per day lube oil treating plant to remove PNA's employing the instant invention, based on engineering calculations, would require approximately 2.4 kJ (2.3 MMBTU/HR) or about one tenth the energy required by the conventional processes to improve the quality indices of the lube oil feedstock.

The present invention is a process for the recovery of aromatic hydrocarbons from a mixture thereof with non-aromatic hydrocarbons. The process comprises a series of sequential steps. The mixture is passed to an extractor wherein the mixture is contacted with a lean solvent stream at extraction conditions including an extraction temperature. A raffinate stream comprising the non-aromatic hydrocarbons and a rich solvent stream comprising the aromatic hydrocarbons are withdrawn from the extractor. A first water stream is admixed with the raffinate stream to provide a raffinate admixture. The raffinate admixture is passed to a raffinate separator to provide a raffinate product stream and a first wet solvent stream. A second water stream is admixed with the rich solvent stream to provide a rich solvent admixture. The rich solvent admixture at or below a low critical solution temperature of the solvent with water is passed to an extract separator to provide a second wet solvent stream and an aromatic product stream. The first wet solvent stream and the second wet solvent stream are combined and the combined wet solvent stream is heated to a separation temperature above the low critical solution temperature of the solvent with water. The heated wet solvent stream is passed to a solvent separator to provide a hot lean solvent stream comprising a reduced amount of water and a third water stream. The hot lean solvent stream is cooled to provide the lean solvent stream. The third water stream is cooled and split to provide the first water stream and the second water stream.

The invention employs a group of solvents that were surprisingly found to exhibit the formation of a low critical solution temperature of the solvent with the solute below which the solute is completely soluble in the solvent. Upon heating the mixture of the solvent and the solute, the solubility of the solute in the solvent is reversed, forming two separate phases, a solvent phase essentially free of solute and a solute phase essentially free of solvent. Some examples of solvents forming this low critical solution temperature with water were discovered to be the following: 2-butoxyethanol, 2-isobutoxyethanol, diethylene glycol monohexyl ether, diethylene glycol monoethyl ether acetate, 2-ethoxyethyl ether, diethylene glycol tert-butyl methyl ether, propylene glycol 1-mono-tert-butyl ether, 50HB55 UCON Fluid, 50HB170 UCON Fluid, 50HB260 UCON Fluid, 50HB5100 UCON Fluid, 1–2 propylene glycol, 1-propyl ether, 1–2 propylene glycol, 2-propyl ether and mixtures thereof. The solvents 50HB55 UCON Fluid, 50HB170 UCON Fluid, 50HB260 UCON Fluid, 50HB5100 UCON Fluid, are lubricating fluids which are available from Union Carbide, Danberry, Conn.

The above mentioned Union Carbide 50HB UCON lubricating fluids may be further identified as linear polymers of ethylene and propylene oxide with the general formula:

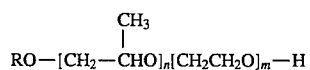

containing equal amounts by weight of oxyethylene (m) and oxypropylene (n) groups, and being water soluble at temperatures below 40° C.

In another embodiment, the invention is a process for the separation a first component from a mixture thereof with a second component comprising a series of steps. The mixture is passed to an extraction zone and contacted therein with a lean solvent stream to selectively extract the first component from the mixture to provide a raffinate stream depleted in the first component and a rich solvent stream enriched in the first component relative to the mixture. The raffinate stream and the rich solvent stream are separately contacted with a solute stream at a temperature which is at or below the formation of a low critical solution temperature of said solvent with said solute, said solute being insoluble with said first and said second components, to provide a raffinate phase comprising the second component, an extract phase comprising the first component, and a solute/solvent phase. The solute/solvent phase is heated to a separation temperature to provide the lean solvent stream and the solute stream. This process may be employed for a variety of separations in the process industry wherein a solvent/solute combination exhibits the low critical solution property and the solute is relatively insoluble in the components of the mixture to be separated by the selective solvent.

BRIEF DESCRIPTION OF THE DRAWING

The drawing represents a schematic flow diagram of the process of the invention wherein a mixture of aromatic and non-aromatic hydrocarbons is separated in an extractor and the resulting raffinate and rich solvent streams are processed with a solvent exhibiting a low critical solution temperature with water.

DETAILED DESCRIPTION OF THE INVENTION

As noted above, historically there has been and continues to be an industrial need for an energy efficient process for the separation of aromatic and non-aromatic hydrocarbons present in mixed hydrocarbon feeds. Naphthas, heating oils, light oils, cracked gasolines, dripolenes, lubricating oils (light distillates to heavy distillates) kerosene and the like, can contain up to 90 percent by weight aromatic-type hydrocarbons., e.g., BTX or polynucleararomatics. The separation of aromatic and non-aromatic hydrocarbons is of particular interest in the dearomatization of crude lube oils. Crude lube oils and lube distillates may comprise PNA's ranging from 1 to 20 wt %, or more preferably comprising from 2 to 5 wt %. The components which make up these hydrocarbon feed streams are well known in the art and they will not be extensively discussed herein except to note that the mixed hydrocarbon feed employed herein may be any petroleum distillate of the common distillation fractions containing one or more aromatics components including: naphthas (virgin or cracked); kerosene; gasoline; heating oils; lubricating oils (light distillates, heavy distillates, bright stock and residual oils); jet fuels; and cycle oils. Preferably, the feed stream is a lube oil fraction such as a light distillates to heavy distillate, bright stock etc. which have boiling points between about 200° C. (400° F.) and about 595° C. (1100° F.).

The aromatic hydrocarbons present in heavy hydrocarbon feeds, e.g., lubricating oils, generally include: alkylbenzenes, indanes, tetralins, indenes, naphthalenes, fluorenes, acenaphthalenes, biphenyls, phenanltrenes, anthracenes, diacenaphthalenes, pyrenes, chripenes, diaceanthrancenes, benzpyrenes and other various aromatic feed components.

The instant process uses extraction with a group of aromatic selective solvents which exhibit a unique property which is based on the solubility temperature profile of the solvent with water. Examples of these solvents include 2-butoxyethanol, 2-isobutoxyethanol, diethylene glycol monohexyl ether, diethylene glycol monoethyl ether acetate, 2-ethoxyethyl ether, diethylene glycol tert-butyl methyl ether, propylene glycol 1-mono-tert-butyl ether, 50HB55 UCON Fluid, 50HB170 UCON Fluid, 50HB260 UCON Fluid, 50HB5100 UCON Fluid, 1-2 propylene glycol, 1-propyl ether, 1-2 propylene glycol, 2-propyl ether and mixtures thereof. These solvents were discovered to have a unique property called a lower critical solution temperature (LCST) with water. Unlike other solvents heretofore employed in aromatic extraction processes, in which their solubility in water increases with temperature until an upper critical solution temperature is reached at which only one phase exists, the LCST solvents are soluble in water at low temperatures and become insoluble in water as they are heated. Because hydrocarbons, especially aromatic hydrocarbons also are insoluble in water, these LCST solvents can provide a more energy efficient process which does not require a distillation step to separate the LCST solvent from the solute or water phase.

Using the LCST property, a process was formulated which effectively swings the amount solute in order to perform the separation of the aromatic phase from the solvent and uses a temperature swing to separate the solvent from the solute or water phase. In the process, a mixed hydrocarbon feed containing aromatic compounds and non-aromatic compounds is contacted in a liquid/liquid extractor with a dry lean solvent, preferably containing less than about 40 wt % water and more preferably containing from about 0.5 to about 25 wt % water. The extraction step takes place at a relatively low extraction temperature, preferably ranging from about 20° C. to about 150° C., and a pressure such that all of the components and the lean solvent remain in the liquid phase. A raffinate stream comprising the non-aromatic compounds is withdrawn from the top of the extractor and a rich solvent stream comprising the aromatic compounds and the LCST solvent is removed from the bottom of the extractor. A sufficient amount to water, or solute, is then admixed separately with the raffinate and rich solvent streams at a temperature which is at or below a low critical solution temperature with the solute such that the solvent becomes soluble in the solute while the hydrocarbon phase becomes insoluble in the solvent solute mixture. The admixtures are separately decanted to provide a hydrocarbon phase which is essentially free of solvent, and a solute phase comprising the solvent. The hydrocarbon phase may be optionally washed with the solute in a solute wash column to remove further traces of the solvent. The solute/solvent mixture is heated to a separation temperature at which point the solvent becomes insoluble in the solute and is then separated to produce a solute free lean solvent stream. The heated solvent and solute mixture is heated by indirect heat exchange with the cold solvent/solute mixtures. Thus, the only energy required for this solute swing process is for heat approaches in the heat exchangers heating the solute/solvent phase to the separation temperature. Preferably the separation temperature ranges from about 10° C. to about 200° C. above the LCST at a pressure sufficient to maintain the streams in the liquid phase. No further distillation or fractionation steps are required to separate the solute and solvent phases to provide the lean solvent stream. Furthermore, with appropriate heat exchange arrangement, the only heat required by the process is to offset heat losses in the swing from the low critical solution temperature to the separation temperature.

DETAILED DESCRIPTION OF THE DRAWING

With reference to the drawing, an aromatic and non-aromatic hydrocarbon mixture is introduced to an extractor 30 in line 1. Within the extractor, the aromatic and non-aromatic hydrocarbon mixture is countercurrently contacted with a lean solvent introduced to the extractor via line 10 at extraction conditions including an extraction temperature ranging from about 20° C. to about 150° C. and an extraction pressure adequate to maintain the mixtures and the lean solvent in the liquid state. The lean solvent is a selective solvent which selectively extracts the aromatic hydrocarbon components from the hydrocarbon mixture and which forms a low critical solution temperature with the solute, water. A rich solvent stream is removed from the extractor 30 by line 3. The rich solvent stream comprises the aromatic components and the solvent. A raffinate stream is withdrawn from the extractor via line 2. The raffinate stream comprises the non-aromatic hydrocarbons and a small amount of solvent in solution. Typically the raffinate stream will contain between about 0.2 wt. % to about 10 wt. % solvent. The raffinate in stream 2 is admixed with a water stream in line 4 to produce a water solvent raffinate mixture in line 5. The water solvent raffinate mixture is passed to a raffinate separator 35 wherein the hydrocarbon phase raffinate is withdrawn in line 6 and a water stream containing essentially all of the solvent removed from the raffinate is withdrawn in line 7. The rich solvent stream in line 3 is similarly admixed with a second water stream in line 8 which provides a sufficient amount of water to affect the complete separation of the solvent phase from the aromatic hydrocarbon phase and the admixture is conveyed via line 9 to the extract separator 40. In the extract separator 40, the solvent phase is withdrawn via line 12 and the aromatic product is withdrawn in line 11. The separation of the hydrocarbon phase from the solvent/solute phase takes place at or below the low critical solution temperature of the solvent with the solute. When the solute is water, preferably this low critical solution temperature with water will range from about 0° C. to about 150° C., and most preferably the low critical solution temperature with water will range from about 20° C. to about 100° C. Following an optional water wash column (not shown) preferably aromatic product will be essentially free of solvent and thus comprise less than about 100 wt. ppm solvent, and most preferably will comprise less than 10 wt. ppm solvent. The wet solvent streams in lines 7 and 12 are combined in line 13 and heated by indirect heat exchange to raise the temperature of the wet solvent stream to a separation temperature. Preferably the separation temperature will range from about 5° C. to about 200° C. above the low critical solution temperature with the solute. This indirect heat exchange may be accomplished by various combination of process streams or as herein provided by splitting the wet solvent stream into a first portion passed by line 14 to exchanger 46, wherein the first wet solvent stream portion 14 is heat exchanged with a first portion of a hot lean solvent in line 21, and the partially heated wet solvent stream is withdrawn from the heat exchanger 46 in line 17. A second portion of the wet solvent stream may be passed via line 15 through heat exchanger 47 to provide a partially heated wet solvent stream which is conveyed by line 16 to line 19 where it is combined with the other partially heated wet solvent stream. The partially heated wet solvent stream 19 is heated in a steam heater 50 to make up for the heat approaches in heat exchangers 46 and 47 and to reach the separation temperature and then passed by line 20 to the solvent separator 45. The hot lean solvent stream is withdrawn in line 21 and a hot water stream is withdrawn in line 22 from the solvent separator 45. The hot water stream in line 22 is passed to heat exchanger 47 wherein the indirect heat exchange with the wet solvent stream 15 occurs and a partially cooled water stream is withdrawn in line 24 and passed to a cooler 48 to provide a cooled water stream in line 25. Preferably the temperature of the cooled water stream ranges from about 0° C. to about 100° C., and most preferably the temperature of the cooled water stream ranges from about 20° C. to about 80° C. The cooled water stream in line 25 is split to provide a first water stream in line 4 and the second water stream in line 8. The hot lean solvent stream 21 which is now dewatered, having less than about 40 wt % water, is passed to heat exchanger 46 where it is partially cooled to provide a partially cooled lean solvent stream in line 23. The partially cooled lean solvent stream is passed to cooler 49 which reduces the temperature of the lean solvent stream to the extraction temperature and provides the lean solvent stream in line 10.

In another embodiment at least a portion of the first water stream in line 4 may be passed to a raffinate wash column (not shown) wherein the raffinate product stream in line 6 is contacted with the portion of the first water stream to provide a washed raffinate product stream and a first water injection stream. The first water injection stream may be admixed with the raffinate stream in line 5 prior to passing the admixture to the raffinate separator. Similarly, at least a portion of the second water stream in line 8 may be passed to an extract wash column (not shown) wherein the aromatic product stream in line 11 is contacted with the portion of the second water stream to provide a washed aromatic product stream. The above water washing steps may be required to reduce solvent carry over and losses into the raffinate and/or aromatic products.

The following examples are provided to illustrate the invention and are not construed as limiting such in any way.

EXAMPLE I

A number of solvents were determined to exhibit a low critical solution temperature with water. In using these solvents, the solute water is soluble in all proportions with the solvent at the lower temperatures. As the temperature is raised, a point is reached in which two phases begin to form. This temperature is called the low critical solution temperature of the mixture. As the temperature of the mixture continues to be raised, the solute becomes less and less soluble in the solvent until the solute and the solvent are almost insoluble in one another. A table showing examples of solvents which exhibit this low critical solution temperature with water for extraction of aromatic hydrocarbons is given in Table 1.

EXAMPLE II

The invention was simulated in a laboratory with static equilibrium experiments. Three volumes of solvent were mixed with one volume, approximately 80 ml, of a kerosene fraction until phase equilibria was obtained. The distribution coefficient of the aromatic fraction between the solvent and the kerosene fraction was determined. The distribution coefficient determined was assumed to be constant for a twelve theoretical stage, countercurrent extraction step. Volumes of water approximately equal to the volume of aromatic-rich solvent and raffinate phases were used to separate the hydrocarbons from the solvent phase on both of these streams. In this fashion, the process steps of the invention were followed with the exception of the water solvent separation steps and the solvent recycle steps to the extractor. Table 2 shows the results of the experiments. The basic solvent mixture employed was UCON 50HB170 which is a lubricant fluid manufactured by Union Carbide Corporation of Danbury, Conn. Runs A through E of Example 2 show that by the use of the solvent having the low critical solution temperature with water, the extraction can be carried out at relatively low temperatures to achieve a significant separation of the aromatics from the feedstock mixture. In all cases, a feed having 30% volume aromatics was used. The extraction temperature ranged from about 50° C. to about 60° C.

Run A employed the basic solvent with 15 vol. % water and achieved a 78.2 vol % yield of raffinate and about a 5 percent reduction of aromatics in the raffinate. Runs B–D, which employed the basic solvent with 15, 20, and 30% ethylene carbonate as a cosolvent showed that increasing the ethylene carbonate at a slightly higher extraction temperature of 60° C., increased the yield of raffinate from 28.9 to 66.5 vol %, with a corresponding increase in the aromatic content of the raffinate from 2.5 to 19.3 percent. Run E showed the basic solvent in combination with the aromatic selective solvent, sulfolane. Runs B–E showed that the yield of raffinate was depressed and the degree of extraction increased by the addition of the cosolvents.

EXAMPLE III

A 5,000 barrel per day lube oil finishing plant employing the process of the instant invention as described herein was determined by engineering calculation to require about 2.42 kJ (2.3 MMBU/HR) of energy to prepare a treated lube oil raffinate with a reduced concentration of aromatic compounds.

below a low critical solution temperature of said solvent with said solute to provide a raffinate hydrocarbon phase, an aromatic hydrocarbon phase, and a solvent/solute phase; and (c) heating said solvent/solute phase to a separation temperature to provide said lean solvent stream and said solute stream.

2. The process of claim 1 further comprising cooling said lean solvent stream prior to step (a).

3. The process of claim 2 wherein said cooling of said lean solvent stream is provided by indirect heat exchange with said solvent/solute phase.

4. The process of claim 3 wherein said separation temperature is above said low critical solution temperature of said solvent with said solute.

5. The process of claim 4 further comprising passing said raffinate hydrocarbon phase to a first solute wash column to

TABLE 1

SOLVENTS THAT EXHIBIT LCST WITH WATER

| COMPOUND NAME | LCST (°C.) | SEPARATION TEMP. (°C.) | PHASE WT % WATER IN FLUID | COMPOSITION WT % FLUID IN WATER |
|---|---|---|---|---|
| 2-Butoxyethanol | 49 | 90 | 40.3 | 9.7 |
| 2-Isobutoxyethanol | 25 | 90 | 29.5 | 5.3 |
| Diethylene Glycol Monohexyl Ether | 12 | 90 | 17.6 | 1.87 |
| Diethylene Glycol Monoethyl Ether Acetate | 44 | 90 | 17.9 | 15.6 |
| 2-Ethoxyethyl Ether | 30 | 90 | 9.06 | 10.5 |
| Diethylene Glycol Tert-butyl Methyl Ether | 20 | 90 | 7.08 | 5.07 |
| Propylene Glycol Mono-tert-butyl Ether | 7.7 | 90 | 12.7 | ~4.84 |
| 50HB55 UCON Fluid (1) | 40 | 100 | ~10 | ~10 |
| 50HB170 UCON Fluid (1) | 40 | 100 | ~10 | ~10 |
| 50HB260 UCON Fluid (1) | 40 | 100 | ~10 | ~10 |
| 50HB5100 UCON Fluid (1) | 40 | 100 | ~10 | ~10 |
| 1-2 Propylene Glycol, 1-Propyl Ether | 34.5 | | | |
| 1-2 Propylene Glycol, 2-Propyl Ether | 42.6 | | | |

(1) Lubricant fluids manufactured by Union Carbide Corp., Danberry, Conn.

TABLE 2

| | SOLVENT USED | EXTRACTION TEMPERATURE | Vol % FEED | AROMATICS IN RAFF | AROMATICS IN EXTRACT | VOL % RAFF YIELD |
|---|---|---|---|---|---|---|
| A | 50HB170 + 15% Water | 50 C. | 30.0 | 24.9 | 48.2 | 78.2 |
| B | 50HB170 + 15% EC | 60 C. | 30.0 | 2.5 | 41.2 | 28.9 |
| C | 50HB170 + 20% EC | 60 C. | 30.0 | 10.4 | 46.6 | 45.9 |
| D | 50HB170 + 30% EC | 60 C. | 30.0 | 19.3 | 51.3 | 66.5 |
| E | 50HB170 + 30% SULF | 60 C. | 30.0 | 8.1 | 48.5 | 45.8 |

EC = Ethylene carbonate
SULF = Sulfolane

I claim:

1. A process for the recovery of aromatic hydrocarbons from a mixture thereof with non-aromatic hydrocarbons comprising:

(a) passing said mixture to an extraction zone wherein said mixture is contacted with a lean solvent stream and withdrawing a raffinate stream comprising said non-aromatic hydrocarbons and a rich solvent stream comprising said aromatic hydrocarbons; (b) separately admixing a solute stream comprising a solute which is insoluble in said aromatic and non-aromatic hydrocarbons with said raffinate and rich solvent streams at or provide a raffinate product essentially free of said solvent and a first solute wash stream.

6. The process of claim 5 further comprising passing said aromatic hydrocarbon phase to a second solute wash column to provide an aromatic product essentially free of solvent and a second solute wash stream.

7. The process of claim 6 further comprising combining said first and second solute wash streams to provide said solute stream.

8. A process for the recovery of aromatic hydrocarbons from a mixture thereof with non-aromatic hydrocarbons comprising:

(a) passing said mixture to an extractor wherein said mixture is contacted with a lean solvent stream at extraction conditions including an extraction temperature and withdrawing a raffinate stream comprising said non-aromatic aromatic hydrocarbons and rich solvent stream comprising said aromatic hydrocarbons;

(b) admixing a first water stream with said raffinate stream to provide a raffinate admixture at or below a low critical solution temperature of the solvent with water and passing said raffinate admixture to a raffinate separator to provide a raffinate product stream and a first wet solvent stream;

(c) admixing a second water stream with said rich solvent stream to provide a rich solvent admixture at or below a low critical solution temperature of the solvent with water and passing said rich solvent admixture to an extract separator to provide a second wet solvent stream and an aromatic product stream; and (d) heating said first wet solvent stream and said second wet solvent stream to a separation temperature above the low critical solution temperature of the solvent with water and passing the heated wet solvent streams to a solvent separator to provide a hot lean solvent stream comprising a reduced amount of water and a third water stream.

9. The process of claim 8 further comprising cooling said hot lean solvent stream to provide said lean solvent stream and cooling and splitting said third water stream to provide said first water stream and said second water stream.

10. The process of claim 9 wherein said lean solvent is selected from the group consisting of 2-butoxyethanol, 2-isobutoxyethanol, diethylene glycol monohexyl ether, diethylene glycol monoethyl ether acetate, 2-ethoxyethyl ether, diethylene glycol tert-butyl methyl ether, propylene glycol 1-mono-tert-butyl ether, 50HB55 UCON Fluid, 50HB170 UCON Fluid, 50HB260 UCON Fluid, 50HB5100 UCON Fluid, 1,2-propylene glycol 1-propyl ether, 1,2-propylene glycol 2-propyl ether, and mixtures thereof.

11. The process of claim 8 wherein the extraction temperature ranges from about 20° C. to about 150° C.

12. The process of claim 8 wherein the hot lean solvent stream comprises less than 40 wt. % water.

13. The process of claim 8 wherein the hot lean solvent stream comprises from about 0.5 to about 25 wt. % water.

14. The process of claim 8 wherein the separation temperature ranges from about 5° C. to about 200° C. above the low critical solution temperature of the solvent with water.

15. The process of claim 8 wherein at least a portion of said hot lean solvent is cooled by indirect heat exchange with said first wet solvent stream and said second wet solvent stream.

16. The process of claim 8 wherein at least a portion of said third water stream is cooled by indirect heat exchange with said first wet solvent stream and said second wet solvent stream.

17. The process of claim 8 wherein said lean solvent forms a low critical solution temperature with water.

18. The process of claim 8 wherein said lean solvent stream comprises less than 10 wt. % hydrocarbons.

19. The process of claim 8 wherein said contacting of the lean solvent is countercurrent to said mixture passing.

20. The process of claim 9 further comprising passing at least a portion of said first water stream to a raffinate wash column and therein contacting the raffinate product stream to provide a washed raffinate product stream and a first water injection stream.

21. The process of claim 20 further comprising admixing said first water injection stream with said raffinate stream.

22. The process of claim 9 further comprising passing at least a portion of said second water stream to an extract wash column and therein contacting the aromatic product stream to provide a washed aromatic product stream and a second water injection stream.

23. The process of claim 22 further comprising admixing said second water injection stream with said rich solvent stream.

24. The process of claim 9 wherein said mixture comprises a crude lube oil.

25. The process of claim 24 wherein said mixture comprises polynuclear aromatics in an amount ranging from about 1 wt % to about 20 wt %.

26. The process of claim 9 wherein said mixture is selected from the group consisting of naphthas, kerosene, heating oils, lubricating oils, jet fuels and cycle oils.

* * * * *